(12) United States Patent
Segawa et al.

(10) Patent No.: US 7,952,712 B2
(45) Date of Patent: May 31, 2011

(54) METHOD FOR DETECTING EQUATORIAL PLANE

(75) Inventors: Susumu Segawa, Tokyo (JP); Yusuke Ebi, Tokyo (JP)

(73) Assignee: Yamatake Corp., Tokyo (JP)

( * ) Notice: Subject to any disclaimer, the term of this patent is extended or adjusted under 35 U.S.C. 154(b) by 321 days.

(21) Appl. No.: 12/406,263

(22) Filed: Mar. 18, 2009

(65) Prior Publication Data

US 2009/0237663 A1    Sep. 24, 2009

(30) Foreign Application Priority Data

Mar. 24, 2008  (JP) .................................. 2008-075863

(51) Int. Cl.
*G01J 4/00*  (2006.01)
(52) U.S. Cl. ....................................................... 356/365
(58) Field of Classification Search .................. None
See application file for complete search history.

(56) References Cited

FOREIGN PATENT DOCUMENTS

| JP | 2003-115743 A | 4/2003 |
|----|---------------|--------|
| JP | 2005-291955 A | 10/2005 |
| JP | 2008-139051 A | 6/2008 |
| JP | 2009085655    | 4/2009 |

*Primary Examiner* — Gregory J Toatley
*Assistant Examiner* — Juan D Valentin
(74) *Attorney, Agent, or Firm* — McDermott Will & Emery LLP

(57) ABSTRACT

To provide a method for detecting the equatorial plane, capable of detecting directly an equatorial plane that has the optical axis as the axis thereof, in a spherical optically uniaxial crystal. The method for detecting the equatorial plane as set forth in a first form of the present invention is a method for detecting an equatorial plane of a spherical member made from a single crystal of an optically uniaxial crystal having birefringence, comprising: a step for causing light to be incident on the spherical member through a polarizer; and a step for observing the isogyre that is structured by the light that is emitted from the spherical member through an analyzer that has a cross-nicol relationship with the polarizer; wherein the isogyre is an isogyre that is observed when the oscillating direction of the polarizer or the analyzer is near to parallel with the optical axis of the spherical member.

3 Claims, 6 Drawing Sheets

_(1)_

METHOD FOR DETECTING EQUATORIAL PLANE

CROSS REFERENCE TO PRIOR APPLICATIONS

The present application claims priority under U.S.C. §119 to Japanese Patent Application No. 2008-075863, filed Mar. 24, 2008. The content of the application is incorporated herein by reference in its entirety.

FIELD OF TECHNOLOGY

The present invention relates to a method for detecting the equatorial plane when, in a spherical optically uniaxial crystal, the optical axis is defined as the axis of the sphere.

BACKGROUND OF THE INVENTION

There is a ball SAW sensor (spherical Surface Acoustic Wave device) that uses the change in the propagation speed depending on the ambient hydrogen concentration when a surface acoustic wave (SAW) propagates on the surface of a sphere made from a single crystal piezoelectric material such as liquid crystal, langasite, $LiNbO_3$, $LiTaO_3$, or the like. (See Japanese Unexamined Patent Application Publication 2003-115743 and Japanese Unexamined Patent Application Publication 2005-291955). When there is excitation of a surface acoustic wave on the surface of the sphere, the surface acoustic wave does not spread out as would a normal wave, but rather travels around a circular region, with a limited width, along the great circle of the sphere, around a specific crystallographic axis, many times, essentially without attenuation. The ball SAW sensor is an extremely sensitive hydrogen sensor because the change in the aforementioned propagation speed increases proportionately with the number of times that the surface acoustic wave has circled the sphere.

FIG. 6 illustrates schematically the structure of the surface acoustic wave device. A comb electrode 12 and a sensitive membrane 13 are formed on a spherical base member 11 made out of a piezoelectric material single crystal. The sensitive membrane 13 is made out of Pd, Ni, Pd—Ni alloy, or the like, that absorbs hydrogen. Because a sensitive membrane 13 that has absorbed hydrogen becomes rigid, causing the speed of propagation of the surface acoustic wave in the sensitive membrane 13 to become faster, this can be used as a hydrogen sensor. Here the comb electrode 12 and the sensitive membrane 13 must be formed in specific locations on the base member 11. Specifically, the comb electrode 12 and the sensitive membrane 13 are formed on the equator that has, as the axis thereof, the optical axis 14 that passes through the center of the sphere (termed simply the "equator," below), as illustrated in FIG. 6. In the specification, the optical axis that passes through the center of the sphere shall be termed simply the "optical axis." In particular, it is necessary to form the comb electrode 12 with high precision, because there is a sharp decline in the sensitivity of the ball SAW sensor when, in particular, the position at which the comb electrode 12 is inaccurate. Note that piezoelectric materials such as liquid crystal, langasite, $LiNbO_3$, $LiTa_3$, and the like are optically uniaxial crystals, and thus possess a single optical axis.

Here, the optical axis 14, for example, is detected in order to determine the position wherein the comb electrode 12 is to be formed. The comb electrode 12 is formed at a position that is rotated by 90° from the detected optical axis 14, or in other words, on the equator. The sensitivity of the device is reduced, and uniform quality cannot be maintained, if the position wherein the comb electrode 12 is formed is not precise. Because of this, there is the need to detect the optical axis 14 accurately, and the methods for detecting the optical axis described in Japanese Patent Application 2006-322993 and Japanese Patent Application 2007-253006 have been used by the authors. The optical axis can be detected easily and accurately through these methods.

As described above, it is necessary to specify the equator from the detected optical axis 14, and necessary to form the comb electrode 12 thereon. Specifically, after detecting the optical axis 14 of a base member 11 that has a diameter of 1 mm, the base member 11 is held and transferred to the next process, and in the next process, the comb electrode 12 is formed in a position that is 90° from the detected optical axis 14. In this case, the error in each process is cumulative, and thus there is the danger that the position at which the comb electrode 12 is formed may not be accurate.

The object of the present invention is to provide a method for detecting the equatorial plane, capable of detecting directly an equatorial plane that has the optical axis as the axis thereof, in a spherical optically uniaxial crystal.

SUMMARY OF THE INVENTION

The method for detecting the equatorial plane as set forth in an embodiment of the present invention is a method for detecting an equatorial plane of a spherical member made from a single crystal of an optically uniaxial crystal having birefringence, comprising: a step for causing light to be incident on the spherical member through a polarizer; and a step for observing the isogyre that is structured by the light that is emitted from the spherical member through an analyzer that has a cross-nicol relationship with the polarizer; wherein the isogyre is an isogyre that is observed when the oscillating direction of the polarizer or the analyzer is near to parallel with the optical axis of the spherical member.

A method for detecting an equatorial plane as set forth in another embodiment of the present invention is characterized by light that is emitted from the spherical member being light that is reflected within the spherical member, in the form of the invention described above.

A method for detecting an equatorial plane as set forth in a further embodiment of the present invention is characterized the spherical member being made out of liquid crystal, in a form of the invention described above.

The present invention enables the provision of a method for detecting the equitorial plane, capable of detecting directly an equatorial plane that has the optical axis as the axis thereof, in a spherical optically uniaxial crystal.

DETAILED DESCRIPTION OF THE INVENTION

A form of embodiment of the present invention will be described below. Note, however, that the present invention is not limited to the form of embodiment set forth below. Additionally, for clarity in the explanation, the description and drawings below have been abbreviated and simplified as appropriate.

Figure 1:
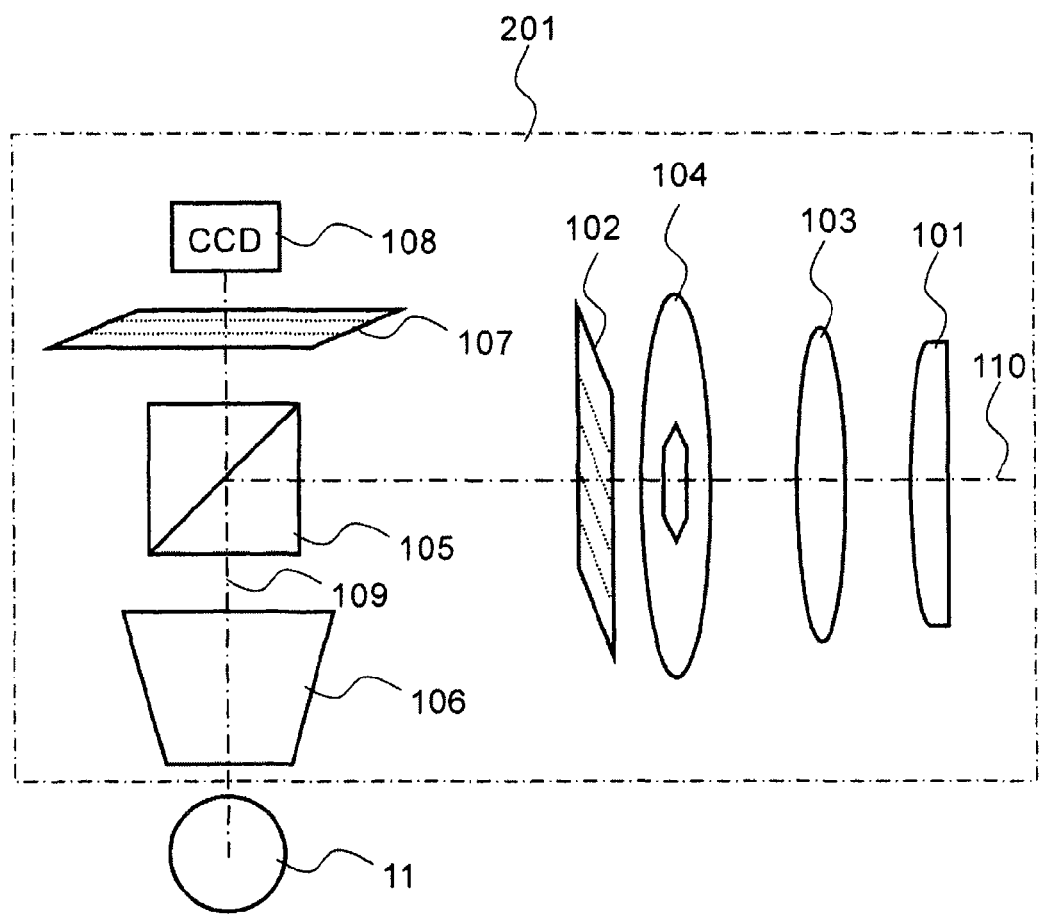
FIG. 1 is a schematic diagram illustrating the optics system in an optical axis measuring device according to a form of embodiment according to the present invention.

The method for detecting the equatorial plane, having, as the axis thereof, the optical axis of a spherical member made out of an optically uniaxial single crystal according to the present form of embodiment of the present invention will be explained using FIG. 1. Note that in the present specification the "equatorial plane" refers to the plane that includes the equator when the axis thereof is the optical axis. The optics system for measurement will be explained first. FIG. 1 is a diagram illustrating schematically the structure of the optics system for measurement in relation to the present form of embodiment. The optics system for measurement in relation to the present form of embodiment is provided with a light source 101, a polarizer 102, a red filter 103, an aperture stop 104, a half mirror 105, an object lens 106, an analyzer 107, and a CCD camera 108, as illustrated in FIG. 1. Specifically, a polarizing microscope is provided with this type of structure.

As is illustrated in FIG. 1, the optics system is of a reflective type. Specifically, the light source 101, the polarizer 102, the red filter 103, the aperture stop 104, and the half mirror 105 that structure an illumination system are arranged in a line in the horizontal direction. On the other hand, the object lens 106, the half mirror 105, the analyzer 107, and the CCD camera 108, which structure an observation system, are arranged in a line in the vertical direction. That is, the optical axis 110 of the illumination system and the optical axis 109 of the observation system have a perpendicular location relationship. Here the half mirror 105 is positioned at the intersection between the optical axis 109 of the observation system and the optical axis 110 of the illumination system Note that the illumination system and the observation system are not limited to this structure, but rather may be structured with the incident light and the emitted light in the same region.

The object to be measured is the base member 11 of the acoustic surface wave device, and is positioned below the object lens 106. The base member 11 is a spherical member made out of a single crystal having birefringence. Liquid crystal, langasite, $LiNbO_3$, $LiTaO_3$, and the like, can be listed as specific substances from which to form the base member 11. Additionally, a photosensitive resist may be coated in a uniform thin layer onto the surface of the base member 11 in order to mark the equator. Note that while in the ball SAW sensor usually a base member 11 having a diameter of between about 1 and 10 mm was used, in the method for detecting the equatorial plane as set forth in the present invention there is no limitation on the diameter.

First the light that is emitted by the light source 101 passes through the red filter 103 to remove the ultraviolet light that would harden the resist on the surface of the base member 11. Then a beam, which is narrowed by the aperture stop 104, is formed into a linearly polarized beam by passing through the polarizer 102. The beam that goes vertically downward from the half mirror 105 passes through the object lens 106 to be incident on the base member 11. The beam that is reflected at the base member 11 is again incident on the object lens 106, and thereafter, the beam that passes through the half mirror 105 passes through the analyzer 107, which is disposed in the cross-nicol direction from the polarizer 102, to be observed using the CCD camera 108.

Here the observation is performed by placing the base member 11, which is made out of an optically uniaxial crystal, between the polarizer 102 and the. analyzer 107, which have the aforementioned cross-nicol relationship. When the optical axis of the base member 11 is near to being parallel with the oscillating direction of the polarizer 102 or the analyzer 107, then a cross-shaped (sometimes termed a "diamond-shaped") isogyre is observed. This isogyre shall be termed the "equatorial plane isogyre," below. The equatorial plane isogyre is observed most clearly when the optical axis of the base member 11 is parallel with the oscillating direction of the polarizer 102 or the analyzer 107, so that the direction of the cross shape or the direction of the diamond shape matches the oscillating direction of the polarizer 102 or the analyzer 107. Typically, interference of polarized light is accompanied by observations of two phenomena: the isogyre and the interference fringes; however, the equatorial plane isogyre is not accompanied by interference fringes because the interference is weak. The present inventors were the first to identify this equatorial plane isogyre.

On the other hand, when the optical axis of the base member 11 approaches the direction of the optical axis of the observation system, the well-known concentric interference fringes and the cross-shaped isogyre that intersect in the center thereof (hereinafter termed the "optical axis isogyre") are observed. Consequently, it is possible to discriminate between the equatorial plane isogyre and the optical axis isogyre. Note that although the present invention is not limited to the reflective type, in the reflective type the entire image of the equatorial plane isogyre can be observed easily, and thus the reflective type is preferred. On the other hand, the transmission type is preferred when one wishes to magnify the equatorial plane isogyre for observation.

Furthermore, given the above, after the equatorial plane has been detected, it is possible to illuminate the equator, which is positioned on the observation side, with epi-illumination, to cause a photosensitive reaction in the resist, to mark the equator.

Figure 2:
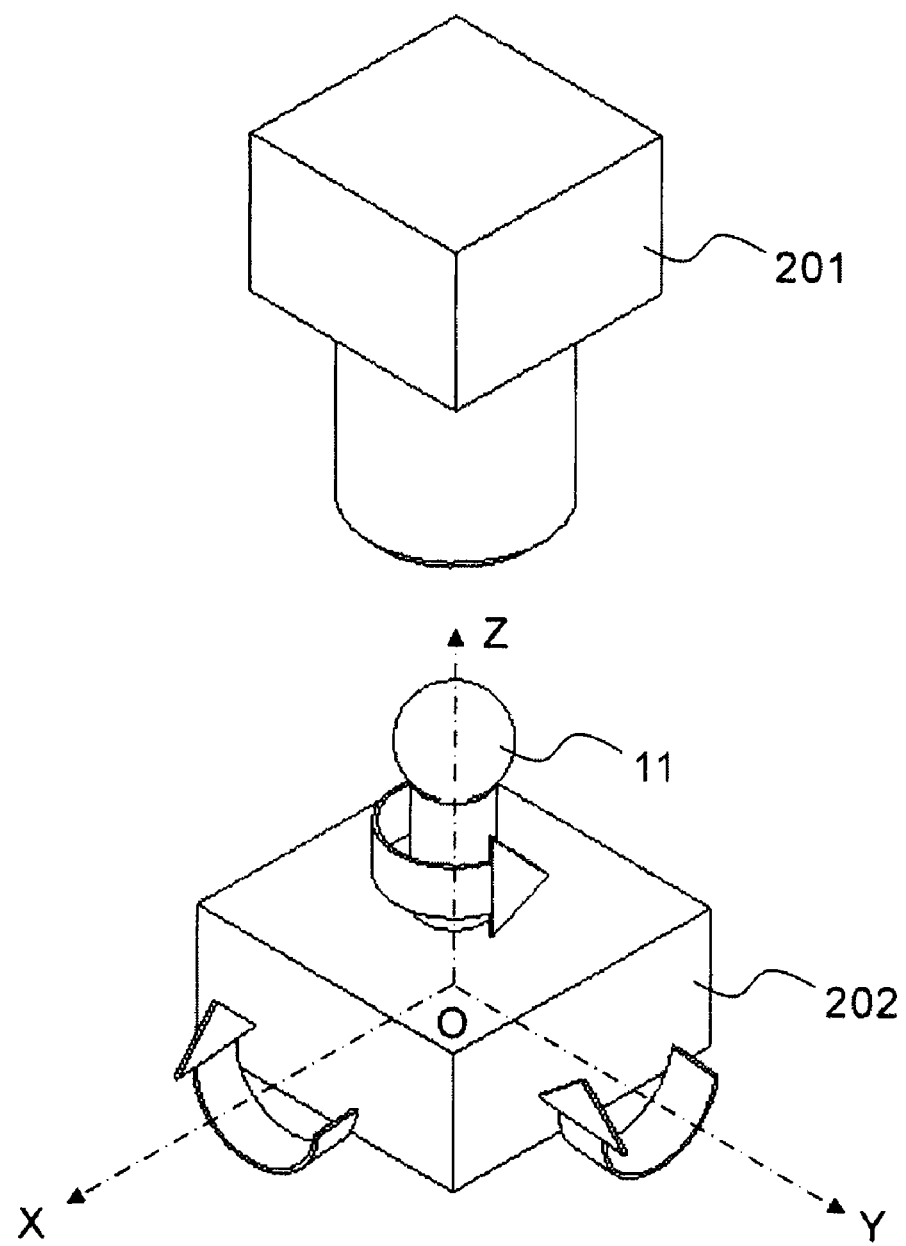
FIG. 2 is a schematic diagram illustrating an optical axis measuring device according to an example of embodiment according to the present invention.

Here, as illustrated in FIG. 2, an equatorial plane measuring device as set forth in the present example of embodiment according to the present invention is provided with a ball positioning unit 202 in addition to the equatorial plane detecting unit 201 as explained in detail using FIG. 1. Here the equatorial plane detecting unit 201 is disposed above the base member 11 in the vertical direction. Additionally, the ball positioning unit 202 holds the base member 11 from the bottom side in the vertical direction. Note that the present invention is not limited to this structure, but rather, for example, the equatorial plane detecting unit 201 may be positioned at an upper oblique and the ball positioning unit 202 may be positioned at the lower oblique opposite thereof.

The ball positioning unit 202, as illustrated in FIG. 2, is capable of rotational motion around the X, Y, and Z axes. It is also capable of translational motion in the X, Y, and Z axial directions. The base member 11 can be positioned in any given position by the ball positioning unit 202, and the direction of the optical axis of the base member 11 can be adjusted to any given direction.

Specifically, the ball positioning unit 202 is operated while the isogyre is observed by the equatorial plane detecting unit 201, as illustrated in FIG. 2, for example. The equatorial plane of the base member 11 can be caused to be parallel with the vertical axis (the Z axis in the drawing), or in other words, with the optical axis of the equatorial plane detecting unit 201. Doing so makes it possible to detect the position of the equator with accuracy.

Next the observed changes in the isogyre image of the equatorial plane will be explained using FIG. 3 through FIG. 5. The drawings in the rectangular frames in FIGS. 3(a) through (c) are image diagrams of equatorial plane isogyres. Diagrams modeling the orientations of the base member 11 are provided under the corresponding figures that are in the rectangular frames. These circles indicate the orientation of the base member 11. The optical axis 14 of the base member 11 is shown in the circles by the arrow, and the equatorial plane 15 is shown by the line segment or the ellipse.

Additionally, between the three diagrams in FIGS. 3(a) through (c), the XYZ coordinate axes of the optics system/observation system are illustrated schematically. Here the X axis is coincident with the oscillating direction of the polarizer, the Y axis is coincident with the oscillating direction of the analyzer, and the Z axis is coincident with the optical axis of the observation system.

First let us consider FIG. 3(b) as the reference. In FIG. 3(b), the Y direction, or in other words, the oscillating direction of the analyzer, is parallel with the optical axis 14 of the base member 11. Because of this, the equatorial plane is parallel to the XZ plane. In this case, the diamond-shaped equatorial plane isogyre image 16 will be observed most clearly. This shows schematically that the central portion will be observed to be dark and the peripheral portion will be observed to be light when the cross-shaped directions or diamond-shaped directions are coincident with the oscillating directions of the polarizer 102 or the analyzer 107.

Figure 3:
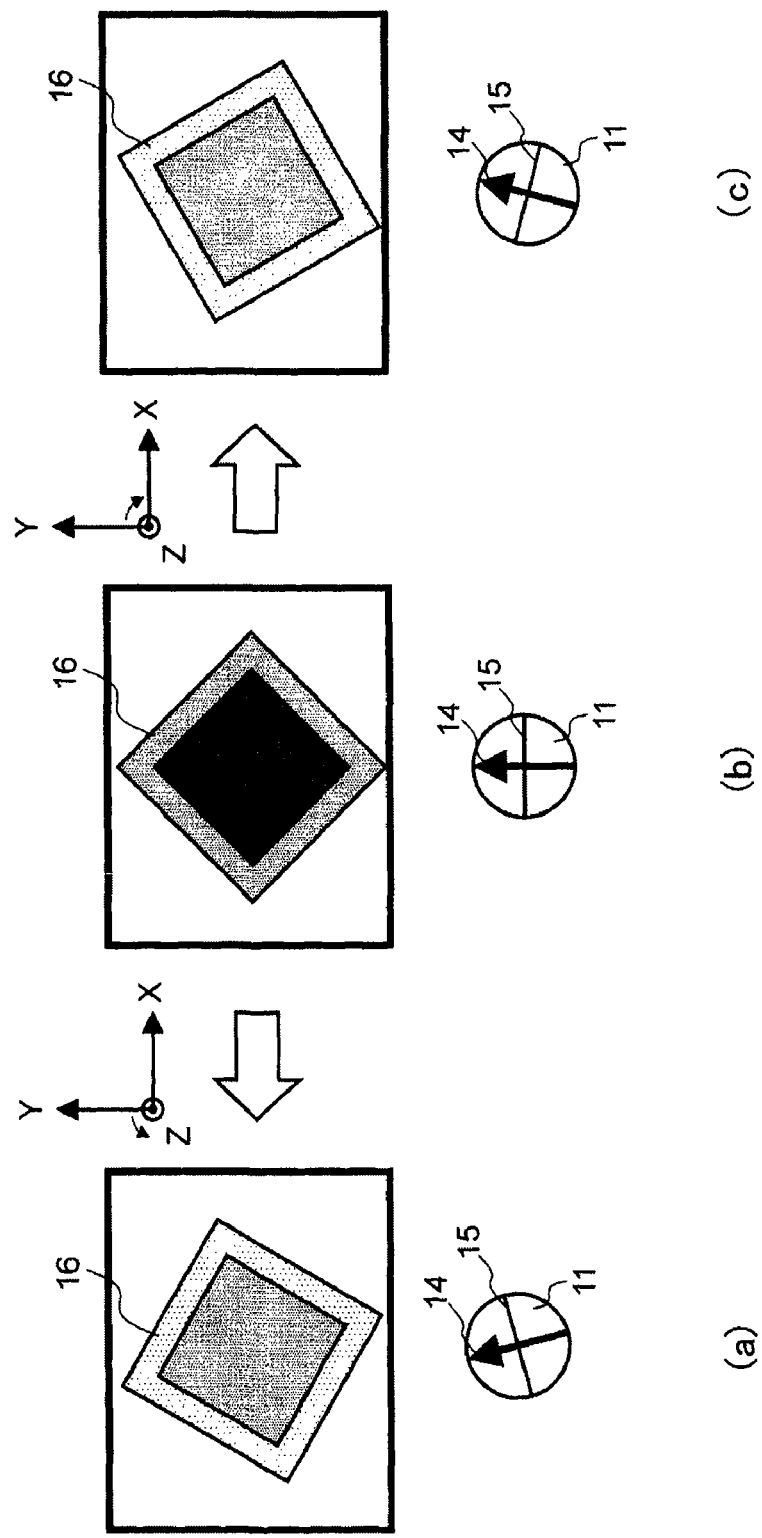
FIG. 3 is a schematic diagram illustrating the change in the isogyre image when there is a rotation of the base member.

In FIG. 3, with FIG. 3(b) as the reference, the isogyre image 16 will show a change when the base member 11 is rotated around the Z axis. FIG. 3(a) illustrates the case wherein there has been a rotation from the X axial direction to the Y axial direction around the Z axis. As is illustrated in FIG. 3(a), the isogyre image 16 also rotates in a rotational direction relative to FIG. 3(b). Additionally, because the optical axis 14 of the base member 11 ceases to be parallel to the Y axis, or in other words, to the oscillating direction of the analyzer (and, at the same time, the equatorial plane 15 ceases to be parallel to the XZ plane), the color of the isogyre image 16 will fade sharply when compared to FIG. 3(b).

On the other hand, FIG. 3(c) illustrates the case wherein there has been a rotation from the Y axial direction to the X axial direction around the Z axis. As illustrated in FIG. 3(c), the isogyre image 16 also rotates in a rotational direction relative to FIG. 3(b). Furthermore, as with the case in FIG. 3(a), because the optical axis 14 of the base member 11 ceases to be parallel to the Y axis, or in other words, to the oscillating direction of the analyzer (and, at the same time, the equatorial plane 15 ceases to be parallel to the XZ plane), the color of the isogyre image 16 will fade sharply when compared to FIG. 3(b).

Figure 4:
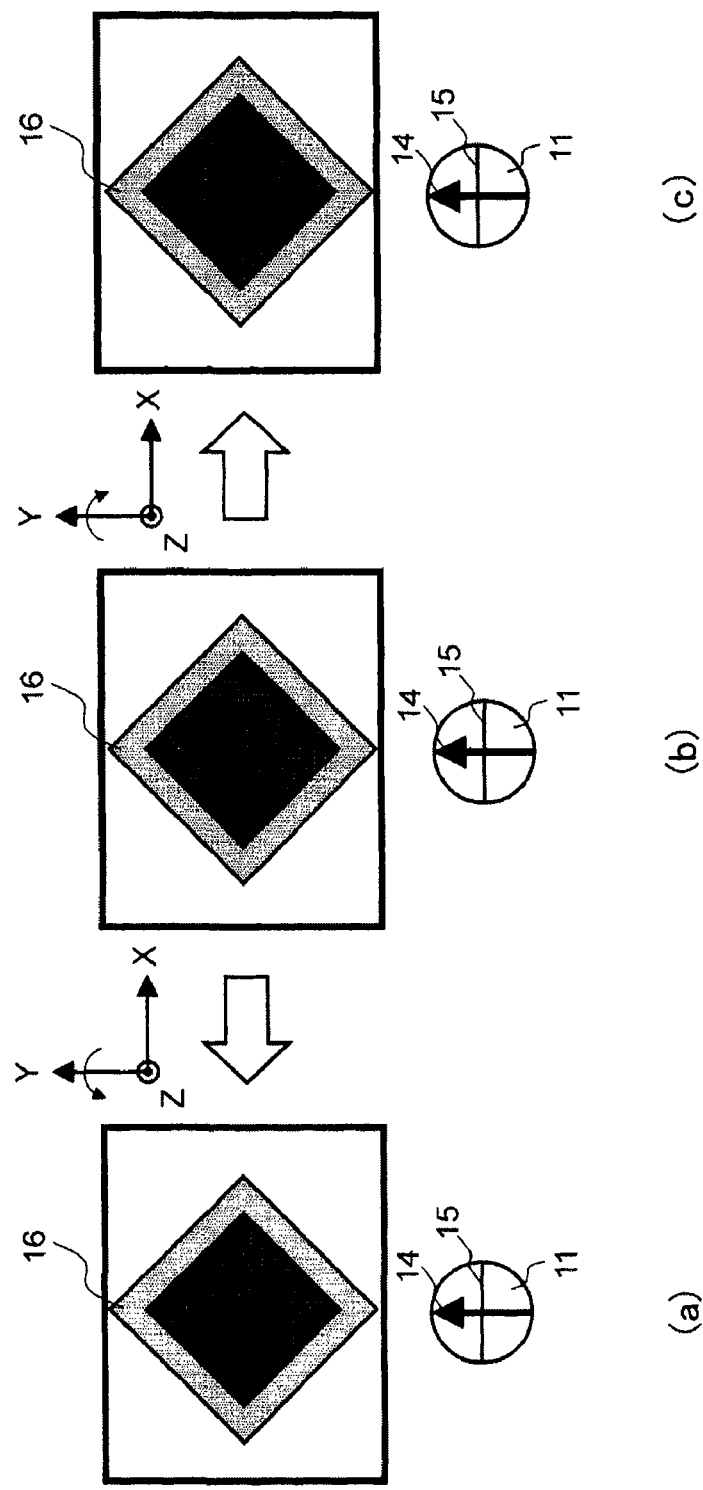
FIG. 4 is a schematic diagram illustrating the change in the isogyre image when there is a rotation of the base member.

FIG. 4 will be explained next. FIG. 4(b) can be considered to be the reference in FIG. 4 as well. Here FIG. 4(b) and FIG. 3(b) are identical diagrams. FIG. 4 illustrates the change in the isogyre image 16 when the base member 11 has been rotated around the Y axis, using FIG. 4(b) as the reference.

FIG. 4(a) illustrates the case wherein there has been a rotation from the X axial direction to the Z axial direction around the Y axis. As is illustrated by the circle in FIG. 4(a), even though there is a rotation around the Y axis, there is no change in the optical axis 14 of the base member 11 being parallel to the Y axis, or in other words, being parallel to the oscillating direction of the analyzer (and, at the same time, there is no change to the equatorial plane 15 being parallel to the XZ plane). Because of this, there is no change relative to FIG. 4(b). On the other hand, FIG. 4(c) illustrates the case wherein there is a rotation from the Z axial direction to the X axial direction around the Y axis. For the same reasons as in the case in FIG. 4(a), there is no change relative to FIG. 4(b).

Figure 5:
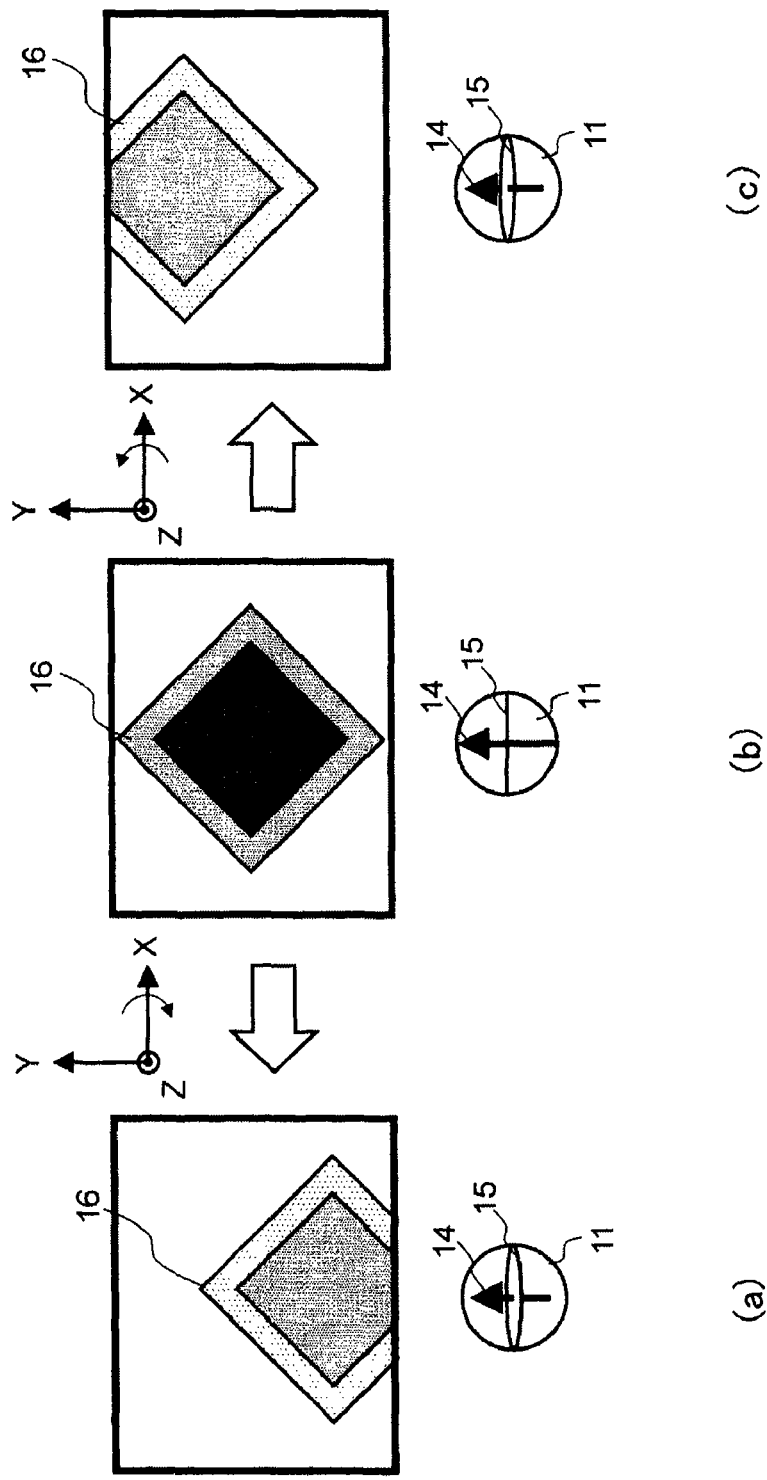
FIG. 5 is a schematic diagram illustrating the change in the isogyre image when there is a rotation of the base member.
Figure 6:
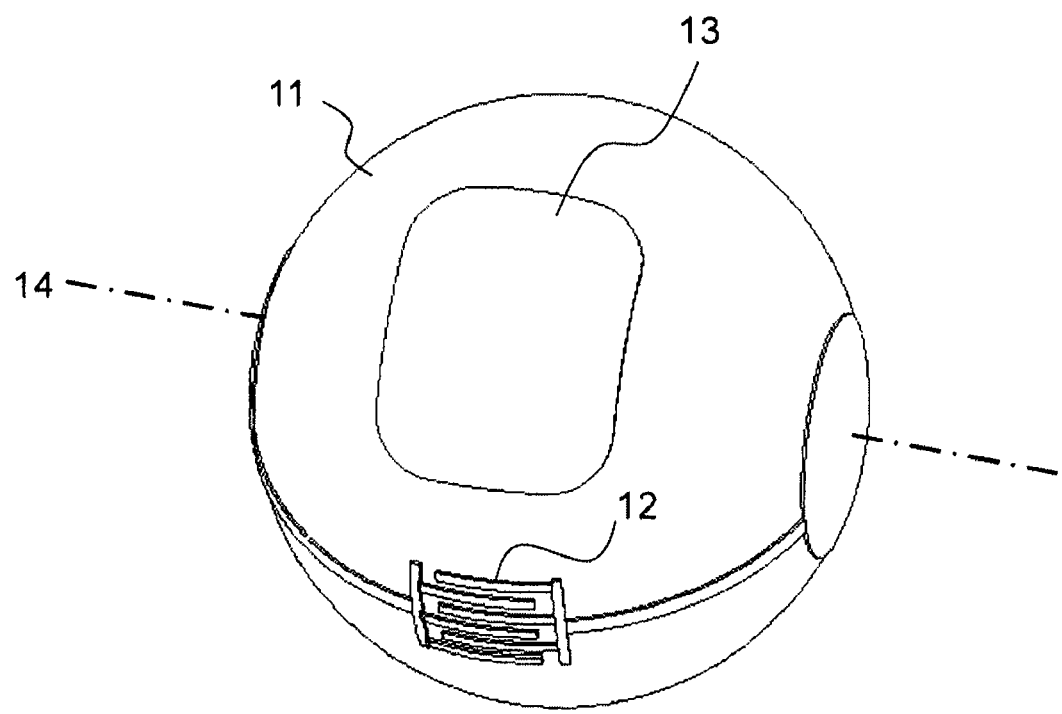
FIG. 6 is a schematic diagram illustrating the structure of a ball SAW sensor.

FIG. 5 will be explained next. In FIG. 5, FIG. 5(b) can also be considered to be the reference. Here FIG. 5(b) is identical to FIG. 3(b) and FIG. 4(b). FIG. 5 illustrates the change in the isogyre image 16 when there is rotation of the base member 11 around the X axis.

FIG. 5(a) illustrates the case wherein there has been a rotation from the Y axial direction to the Z axial direction around the X axis. As is shown in FIG. 5(a), the isogyre image 16 also moves in a translational direction relative to FIG. 5(b). Because of this, the isogyre image 16 moves in the negative Y axial direction relative to that in FIG. 5(b). Additionally, because the optical axis 14 of the base member 11 ceases to be parallel with the Y axis, that is, the oscillating direction of the analyzer (and, at the same time, the equatorial plane 15 ceases to be parallel with the XZ plane), the color of the isogyre image 16 will fade sharply when compared to FIG. 3(b).

On the other hand, FIG. 5(c) illustrates the case wherein there has been a rotation from the Z axial direction to the Y axial direction around the X axis. As is illustrated in FIG. 5(c), the isogyre image 16 moves in a translational direction relative to FIG. 5(b). Because of this, the isogyre image 16 moves in the positive Y axial direction relative to that in FIG. 5(b). Also, as with FIG. 5(a), because the optical axis 14 of the base member 11 ceases to be parallel with the Y axis, or in other words, with the oscillating direction of the analyzer (and, at the same time, the equatorial plane 15 ceases to be parallel with the XZ plane), the color of the isogyre image 16 will fade sharply when compared to FIG. 3(b).

As described above, it is possible to detect the equatorial plane directly but observing the equatorial plane isogyre. This makes it possible to form the comb electrode accurately on the equator. Note that the detection can be performed identically in the case wherein the X axis is the oscillating direction of the analyzer and the Y axis is the oscillating direction of the polarizer.

The invention claimed is:

1. A method for detecting an equatorial plane of a spherical member made from a single crystal of an optically uniaxial crystal having birefringence, comprising the steps of:
    causing light to be incident on the spherical member through a polarizer; and
    observing a isogyre that is structured by the light that is emitted from the spherical member through an analyzer that has a cross-nicol relationship with the polarizer; wherein
    the isogyre is an isogyre that is observed when the oscillating direction of the polarizer or the analyzer is near to parallel with the optical axis of the spherical member.

2. A method for detecting an equatorial plane as set forth in claim 1 wherein the light that is emitted from the spherical member is light that has been reflected within the spherical member.

3. A method for detecting an equatorial plane as set forth in claim 1, wherein the spherical member is made from liquid crystal.

* * * * *